(12) United States Patent
Banov

(10) Patent No.: US 9,775,872 B2
(45) Date of Patent: *Oct. 3, 2017

(54) TOPICAL PHARMACEUTICAL BASES FOR PREVENTING VIRAL DISEASES

(71) Applicant: Professional Compounding Centers of America (PCCA), Houston, TX (US)

(72) Inventor: Daniel Banov, Sugar Land, TX (US)

(73) Assignee: Professional Compounding Centers of America, Houston, TX (US)

( * ) Notice: Subject to any disclaimer, the term of this patent is extended or adjusted under 35 U.S.C. 154(b) by 106 days.

This patent is subject to a terminal disclaimer.

(21) Appl. No.: 14/831,112

(22) Filed: Aug. 20, 2015

(65) Prior Publication Data

US 2016/0051607 A1 Feb. 25, 2016

Related U.S. Application Data

(60) Provisional application No. 62/039,789, filed on Aug. 20, 2014.

(51) Int. Cl.
| | | |
|---|---|---|
| *A61K 36/00* | (2006.01) |
| *A61K 36/32* | (2006.01) |
| *A61K 31/015* | (2006.01) |
| *A61K 31/20* | (2006.01) |
| *A61K 36/47* | (2006.01) |
| *A61K 9/00* | (2006.01) |

(52) U.S. Cl.
CPC ............ *A61K 36/32* (2013.01); *A61K 9/0014* (2013.01); *A61K 31/015* (2013.01); *A61K 31/20* (2013.01); *A61K 36/47* (2013.01)

(58) Field of Classification Search
None
See application file for complete search history.

*Primary Examiner* — Qiuwen Mi
(74) *Attorney, Agent, or Firm* — David G. Woodral; Scott R. Zingerman; Gable Gotwals

(57) ABSTRACT

The present disclosure refers to topical pharmaceutical bases that possess antiviral properties. Further, these topical pharmaceutical bases are employed for preventing a patient to be infected by viral diseases. The topical pharmaceutical bases include Amazonian oils and resins, such as pracaxi oil and breu-branco resin. The synergistic effect of pracaxi oil combined with breu-branco resin results in a highly effective antiviral treatment. Suitable active pharmaceutical ingredients (APIs) can be incorporated to the topical pharmaceutical bases to formulate topical pharmaceutical compositions, which improve antiviral effects. The synergistic effect provided by the combination of pracaxi oil and breu-branco resin enables lower dosage requirements of the associated APIs when topical pharmaceutical compositions are employed for preventing viral diseases.

7 Claims, No Drawings

TOPICAL PHARMACEUTICAL BASES FOR PREVENTING VIRAL DISEASES

CROSS-REFERENCE TO RELATED APPLICATIONS

This application claims priority to U.S. Provisional application Ser. No. 62/039,789, filed Aug. 20, 2014, which is hereby incorporated by reference herein.

BACKGROUND

Field of the Disclosure

The present disclosure relates generally to pharmaceutical compositions, and more particularly, to topical pharmaceutical bases including natural components for preventing viral diseases.

Background Information

Common colds, acute viral infections usually caused by rhinoviruses, are the most common acute illnesses in the United States and account for about one-half of all lost school and work days. Viral infections, such as influenza and rhinoviral infections, cannot only be unpleasant disease conditions in normal individuals, but in certain "at risk" groups represent a serious threat to their health.

In some countries, people have begun to use face masks as a means of protection against respiratory infections. Face masks are effective to prevent entry of pathogens into the respiratory system. However, the use of face masks is generally impractical, inefficient and socially unappealing.

It has been found that applying an antiviral composition to the nasal cavity can help to prevent viral infections. Therefore, there is a need for improved methods for protection against viral diseases, especially when applied to the nasal cavity.

SUMMARY

The present disclosure refers to topical pharmaceutical bases that possess antiviral properties. In some embodiments, the topical pharmaceutical bases are employed for preventing viral transmission via nasal mucosa. In these embodiments, the topical pharmaceutical bases are administered to a patient topically to the nasal mucosa, thereby inhibiting the virus pathogenesis. Further to these embodiments, the topical pharmaceutical bases work as barriers, where viruses are trapped and eradicated.

In some embodiments, the topical pharmaceutical bases include natural components from the Amazon forest. In these embodiments, the topical pharmaceutical bases include pracaxi oil and breu-branco resin. Further to these embodiments, aforementioned natural components exhibit antiviral, analgesic, and healing properties.

In an example, the topical pharmaceutical bases include pracaxi oil in a concentration from about 1% w/w to 20% w/w, preferably from about 5% to 10% w/w; and breu-branco in a concentration from about 1% w/w to 20% w/w, preferably from about 5% w/w to 10% w/w.

In other embodiments, the topical pharmaceutical bases include one or more natural components, such as, for example buriti oil, copaiba balsam, bacaba oil, acai oil, ojon oil, andiroba oil, murumuru butter, and/or tucuma oil, among others. In these embodiments, aforementioned natural components improve skin penetration as well as healing properties.

Further to these embodiments, the concentration of each natural component within topical pharmaceutical bases is from about 1% w/w to 20% w/w, more preferably about 5% w/w.

In some embodiments, the topical pharmaceutical bases are in a dosage form selected from the group consisting of: pharmaceutically acceptable liquids, creams, oils, lotions, ointments, gels, and sprays, among others.

In some embodiments, the topical pharmaceutical bases are directly administered to the nasal cavity. In these embodiments, suitable applicators are employed to administer the topical pharmaceutical bases. In an example, suitable applicators include a swab, brush, cloth, pad, and sponge, among others.

In some embodiments, when the topical pharmaceutical bases are applied to the nasal cavity, the topical pharmaceutical bases deliver a therapeutically effective amount of fatty acids including behenic acid, triterpenes α, β amyrins, and other aforementioned components, which help in the prevention of viral diseases. In these embodiments, the synergistic effect of pracaxi oil combined with breu-branco resin within the topical pharmaceutical bases results in a highly effective antiviral topical formulation, especially when applied to the nasal mucosa.

In other embodiments, active pharmaceutical ingredients (APIs) are incorporated into the topical pharmaceutical bases to formulate topical pharmaceutical compositions. In these embodiments, the synergistic effect provided by the combination of pracaxi oil and breu-branco resin enables lower dosage requirements of the associated APIs when topical pharmaceutical compositions are employed for preventing viral diseases.

In some embodiments, various additives are included to facilitate the preparation of suitable dosage forms. For example, additives include gelling agents, thickening agents, pH adjusters, preservatives, colors, stabilizing agents, antioxidants, and surfactants, among others.

Numerous other aspects, features, and benefits of the present disclosure may be made apparent from the following detailed description.

DETAILED DESCRIPTION

The present disclosure is here described in detail. Other embodiments may be used and/or other changes may be made without departing from the spirit or scope of the present disclosure. The illustrative embodiments described in the detailed description are not meant to be limiting of the subject matter presented here.

Definitions

As used here, the following terms have the following definitions:

"Active Pharmaceutical Ingredients (APIs)" refer to chemical compounds that induce a desired effect, and include agents that are therapeutically effective, prophylactically effective, or cosmeceutical effective.

"Inhibit" refers to decrease, limit, or block the action or function of a process.

"Patient" refers to warm-blooded animals, such as mammals, for example, humans, who are in need of treatment.

"Therapeutically effective amount" refers to the amount of the subject compound that will elicit the biological or medical response of a tissue, system, animal or human that is being sought.

"Treating" and "Treatment" refers to reduction in severity and/or frequency of symptoms, elimination of symptoms and/or underlying cause, prevention of the occurrence of symptoms and/or their underlying cause, and improvement or remediation of damage.

"Viral pathogenesis" refers to the process by which viruses infect and cause disease in a host.

DESCRIPTION OF THE DISCLOSURE

The present disclosure refers to topical pharmaceutical bases that possess antiviral properties. Further, these topical pharmaceutical bases are employed for preventing viral transmission via nasal mucosa.

Formulation

In some embodiments, the topical pharmaceutical bases include natural components from the Amazon forest. In these embodiments, the topical pharmaceutical bases include pracaxi oil and breu-branco resin. Further to these embodiments, aforementioned natural components exhibit antiviral, analgesic, and healing properties.

In an example, the topical pharmaceutical bases include pracaxi oil in a concentration from about 1% w/w to 20% w/w, preferably from about 5% to 10% w/w; and breu-branco in a concentration from about 1% w/w to 20% w/w, preferably from about 5% to 10% w/w.

Pracaxi Oil

Pracaxi oil is obtained from the seed oil of the *Pentaclethara macroloba* tree, or pracaxi tree. The pracaxi tree is a deciduous tree from the legumes family, growing in altitudes below 600 meters in many parts of northern Brazil, Guyana, Trinidad, and parts of Central America, and may reach between about 8 and about 35 meters in height. Pracaxi trees may sometimes be found in wetlands, and are resistant to water logging.

Pracaxi seeds include from about 45% to 48% fat, about 27% to 28% protein, and about 12% to 14% carbohydrates (see Table 1). Pracaxi seed oil includes the highest known natural concentration of behenic acid (about 20%) in a vegetable fat, more than six times higher than in peanut oil, and also includes about 35% of oleic acid. In some cases, pracaxi seed oil may include greater percentages of the aforementioned behenic acid and oleic acid. The oleic acid and lauric acid, contained within pracaxi oil are effective vehicles for delivering drugs through the skin.

TABLE 1

General composition of pracaxi oil.

| Components | Composition % |
|---|---|
| Fat | 45-48 |
| Protein | 27-28 |
| Carbohydrates | 12-14 |

In an example, the fatty acid composition of the pracaxi oil is illustrated below in Table 2. Compositions vary depending on the region and conditions in which the pracaxi tree grows.

TABLE 2

Fatty acid composition of the pracaxi oil.

| Fatty Acids | Carbon Atoms | Composition % |
|---|---|---|
| Lauric | 12:00 | 1.30 |
| Myristic | 14:00 | 1.21 |
| Palmitic | 16:00 | 2.04 |
| Stearic | 18:00 | 2.14 |

TABLE 2-continued

Fatty acid composition of the pracaxi oil.

| Fatty Acids | Carbon Atoms | Composition % |
|---|---|---|
| Oleic | 18:10 | 44.32 |
| Linoleic | 18:20 | 1.96 |
| Linolenic | 18:30 | 2.31 |
| Behenic | 22:00 | 9.67 |
| Lignoceric | 24:00 | 14.81 |

Pracaxi oil has been widely employed within pharmaceutical compositions because of its cosmetic, therapeutic, and medicinal properties. Pracaxi oil is rich in organic acids with antioxidant, antibacterial, antiviral, antiseptic, antifungal, anti-parasitic, and anti-hemorrhagic properties. Because pracaxi oil possesses many of the aforementioned properties, pracaxi oil can be suitable for preventing viral diseases.

TABLE 3

Specifications of the pracaxi oil.

| Indicators | Reference Value |
|---|---|
| Texture | Solid below 18.5° C., liquid viscous texture above this temperature |
| Color | Translucent yellow, yellowish-white when solid |
| Odor | Almost odorless |
| Melting point | 18.5° C. |
| Refractive index (40° C.) | 1.4690 |
| Iodine value | 65-70 g I2/100 g |
| Saponification value | 170-180 mg kOH/g |
| Acid value | 3-5 mg KOH/g |
| Peroxide value | 5-10 mEQ/kg |
| Density (25°) | 0.917 g/cm$^3$ |

Breu-Branco Resin

Breu-branco resin (*Protium heptaphyllum, Burseraceae*) is extracted from an Amazon jungle tree called Almécega. Almécega is a tree that grows in dry forests and is native to most of Brazil. The Almécega trees give off an aromatic fragrance and have a dark red bark. Additionally, Almécega trees grow from about 10 to 20 meters in height, and from about 50 to 60 centimeters in diameter at the base.

When a cut is made in the trunk of Almécega trees, the breu-branco resin exudes. This resin has a white-greenish color and a very pleasant fragrant aroma. Additionally, the breu-branco resin hardens when coming in contact with air. In several areas of Brazil, the resin is collected from the trunk of Almécega trees, and then ground manually after it hardens. Typically, breu-branco resin is collected year-round, but especially in the summer season. After the resin is collected, the resin is dried in the shade and then stored in sacks made of fibers, such as jute. Cuts on an Almécega tree to extract the resin are first made when the tree is about 8 to 10 years old. To harvest the resin of this species sustainably, it is recommended that each Almécega tree receives only about 2 to about 3 cuts per year.

Additionally, yields vary according to the process of extraction. For example, the process of hydro-distillation yields about 11% resin, whereas steam distillation yields about 2.5% resin. The general composition of the resin of breu-branco is provided in Table 4, while the monoterpene composition within the resin of breu-branco is provided in Table 5.

TABLE 4

| Composition of breu-branco resin. | |
|---|---|
| Ingredients | Composition % |
| Resinic acids | 60-75 |
| Terpenes | 10-15 |
| Various substances/water | 5-10 |

TABLE 5

| Composition of breu-branco resin monoterpene. | |
|---|---|
| Monoterpenes | Composition % |
| α-pyrene | 10.50 |
| Limonene | 16.90 |
| α-pheliandrene | 16.70 |
| Terpinolene | 28.50 |
| Others | 27.40 |

Breu-branco resin is often used in Amazonian regions for treating some physical conditions. Breu-branco resin is aromatic and rich in triterpenes α, β amyrins, which possess analgesic and anti-inflammatory properties. In traditional medicine, the resin of breu-branco is suggested for asthma, bronchitis, coughs, headaches stomach aches, liver disorders, memory loss, concentration, motor coordination, for soothing states of agitation and stress, as an anti-inflammatory and analgesic, for wound healing, and as a stimulating agent, among others.

In other embodiments, the topical pharmaceutical bases include one or more natural components, such as, for example buriti oil, copaiba balsam, bacaba oil, acai oil, ojon oil, andiroba oil, murumuru butter, and/or tucuma oil, among others. In these embodiments, aforementioned natural components improve skin penetration as well as healing properties. Further to these embodiments, the concentration of each natural component within topical pharmaceutical bases is from about 1% w/w to 20% w/w, preferably about 5% w/w.

In further embodiments, active pharmaceutical ingredients (APIs) are incorporated into the topical pharmaceutical bases to formulate topical pharmaceutical compositions. In these embodiments, the synergistic effect provided by the combination of pracaxi oil and breu-branco resin enables lower dosage requirements of the associated APIs when topical pharmaceutical compositions are employed for preventing viral diseases.

Administration

In some embodiments, the topical pharmaceutical bases are employed for preventing viral transmission via nasal mucosa. In these embodiments, the topical pharmaceutical bases are administered to a patient's nasal mucosa, thereby inhibiting the virus pathogenesis. Further to these embodiments, topical pharmaceutical bases are used as butter-type formulations and are applied topically to the nasal region to create a barrier, where viruses are trapped and eradicated.

In some embodiments, the topical pharmaceutical bases are in a dosage form selected from the group consisting of: pharmaceutically acceptable liquids, creams, oils, lotions, ointments, gels, and sprays, among others.

In some embodiments, the topical pharmaceutical bases are directly administered to the nasal cavity. In these embodiments, suitable applicators are employed to administer the topical pharmaceutical bases. In an example, suitable applicators include a swab, brush, cloth, pad, and sponge, among others.

In some embodiments, when the topical pharmaceutical bases are applied onto the affected area, the topical pharmaceutical bases a therapeutically effective amount of fatty acids including behenic acid, triterpenes α, β amyrins, and other aforementioned components, which help in the prevention of viral diseases. In these embodiments, the synergistic effect of pracaxi oil combined with breu-branco resin within the topical pharmaceutical bases results in a highly effective antiviral topical formulation, especially when applied to the nasal mucosa.

In some embodiments, various additives are included to facilitate the preparation of suitable dosage forms. For example, additives include gelling agents, thickening agents, pH adjusters, preservatives, colors, stabilizing agents, antioxidants, and surfactants, among others.

While various aspects and embodiments have been disclosed, other aspects and embodiments are contemplated. The various aspects and embodiments disclosed are for purposes of illustration and are not intended to be limiting, with the true scope and spirit being indicated by the following claims.

What is claimed is:

1. A method comprising:

applying a pharmaceutical composition including about 1% w/w to about 95% w/w pracaxi oil, breu-branco resin, and a pharmaceutically effective amount of at least one active pharmaceutical ingredient to the mucosa.

2. The method of claim 1, wherein the pharmaceutical composition comprises about 5% w/w to about 50% w/w breu-branco resin.

3. The method of claim 2, wherein the pharmaceutical composition further comprises at least one natural component selected from the group consisting of about 1% w/w to about 20% w/w buriti oil, about 1% w/w to about 20% w/w copaiba balsam, about 1% w/w to about 20% w/w bacaba oil, about 1% w/w to about 20% w/w acai oil, about 1% w/w to about 20% w/w ojon oil, about 1% w/w to about 20% w/w andiroba oil, about 1% w/w to about 20% w/w murumuru butter, and about 1% w/w to about 20% w/w tucuma oil.

4. The method of claim 2, wherein the pharmaceutical composition comprises about 10% w/w to about 20% w/w pracaxi oil.

5. The method of claim 2, wherein the pharmaceutical composition is selected from the group consisting of a pharmaceutically acceptable liquid, a cream, an oil, a lotion, an ointment, a gel, and a spray.

6. The method of claim 5, wherein the pharmaceutical composition is applied with an applicator selected from the group consisting of a swab, a brush, a cloth, a pad, and a sponge.

7. The method claim 2, wherein the mucosa is nasal mucosa.

* * * * *